(12) United States Patent
Fallin et al.

(10) Patent No.: US 7,811,303 B2
(45) Date of Patent: Oct. 12, 2010

(54) BODILY TISSUE DILATION SYSTEMS AND METHODS

(75) Inventors: T. Wade Fallin, Hyde Park, UT (US); Daniel J. Triplett, Providence, UT (US); Daniel F. Justin, Logan, UT (US)

(73) Assignee: Medicine Lodge Inc, Logan, UT (US)

( * ) Notice: Subject to any disclaimer, the term of this patent is extended or adjusted under 35 U.S.C. 154(b) by 2177 days.

(21) Appl. No.: 10/648,068

(22) Filed: Aug. 26, 2003

(65) Prior Publication Data

US 2005/0080443 A1 Apr. 14, 2005

(51) Int. Cl.
*A61M 29/00* (2006.01)
(52) U.S. Cl. ..................................... 606/191
(58) Field of Classification Search ................ 606/191
See application file for complete search history.

(56) References Cited

U.S. PATENT DOCUMENTS

| | | | |
|---|---|---|---|
| 2,476,216 A * | 7/1949 | Polleau ..................... 248/188.5 |
| 2,707,956 A | 5/1955 | Koff |
| 3,509,883 A | 5/1970 | Dibelius |
| 3,788,318 A | 1/1974 | Kim et al. |
| 3,789,852 A | 2/1974 | Kim et al. |
| 3,811,449 A | 5/1974 | Gravlee et al. |
| 4,449,532 A * | 5/1984 | Storz ........................... 606/191 |
| RE31,855 E | 3/1985 | Osborne |
| 4,629,450 A | 12/1986 | Suzuki et al. |
| 4,686,984 A | 8/1987 | Bonnet |
| 4,738,666 A | 4/1988 | Fuqua |
| 4,772,266 A | 9/1988 | Groshong |
| 4,824,433 A | 4/1989 | März et al. |
| 4,862,891 A * | 9/1989 | Smith ........................... 606/191 |
| 4,899,729 A | 2/1990 | Gill et al. |
| 5,006,113 A * | 4/1991 | Fischer .................. 604/167.04 |
| 5,112,308 A | 5/1992 | Olsen et al. |
| 5,139,511 A | 8/1992 | Gill et al. |
| 5,158,543 A | 10/1992 | Lazarus |
| 5,183,464 A | 2/1993 | Dubrul et al. |
| 5,246,424 A | 9/1993 | Wilk |
| 5,342,384 A | 8/1994 | Sugarbaker |
| 5,472,426 A | 12/1995 | Bonati et al. |
| 5,591,194 A | 1/1997 | Berthiaume |
| 5,601,590 A | 2/1997 | Bonutti et al. |
| 5,685,856 A | 11/1997 | Lehrer |

(Continued)

FOREIGN PATENT DOCUMENTS

EP 0 390 528 B1 6/1996

*Primary Examiner*—Darwin P Erezo
*Assistant Examiner*—Melissa Ryckman
(74) *Attorney, Agent, or Firm*—Peter K. Johnson; G. Jo Hays; James Larson

(57) ABSTRACT

A dilating system for dilating bodily tissue includes a elongate tubular first dilator and a elongate tubular second dilator. The second dilator has an outer diameter greater than the outer diameter of the first dilator, the first dilator being configured to be received within the second dilator. In one embodiment, a first mating member is formed on the exterior surface of the first dilator while a second mating member is formed on the interior surface of the second dilator. The first mating member engages with the second mating member when the second dilator is passed over the first dilator so as to cause the second dilator to travel along a fixed path relative to the first dilator.

23 Claims, 12 Drawing Sheets

U.S. PATENT DOCUMENTS

| | | | |
|---|---|---|---|
| 5,718,266 A * | 2/1998 | Bondioli | 138/114 |
| 5,846,259 A | 12/1998 | Berthiaume | |
| 5,967,970 A | 10/1999 | Cowan et al. | |
| 6,159,179 A | 12/2000 | Simonson | |
| 6,186,986 B1 | 2/2001 | Berg et al. | |
| 6,245,052 B1 | 6/2001 | Orth et al. | |
| 6,277,094 B1 | 8/2001 | Schendel | |
| 6,360,750 B1 | 3/2002 | Gerber et al. | |
| 7,008,431 B2 * | 3/2006 | Simonson | 606/86 R |
| 2004/0059339 A1 * | 3/2004 | Roehm et al. | 606/90 |

* cited by examiner

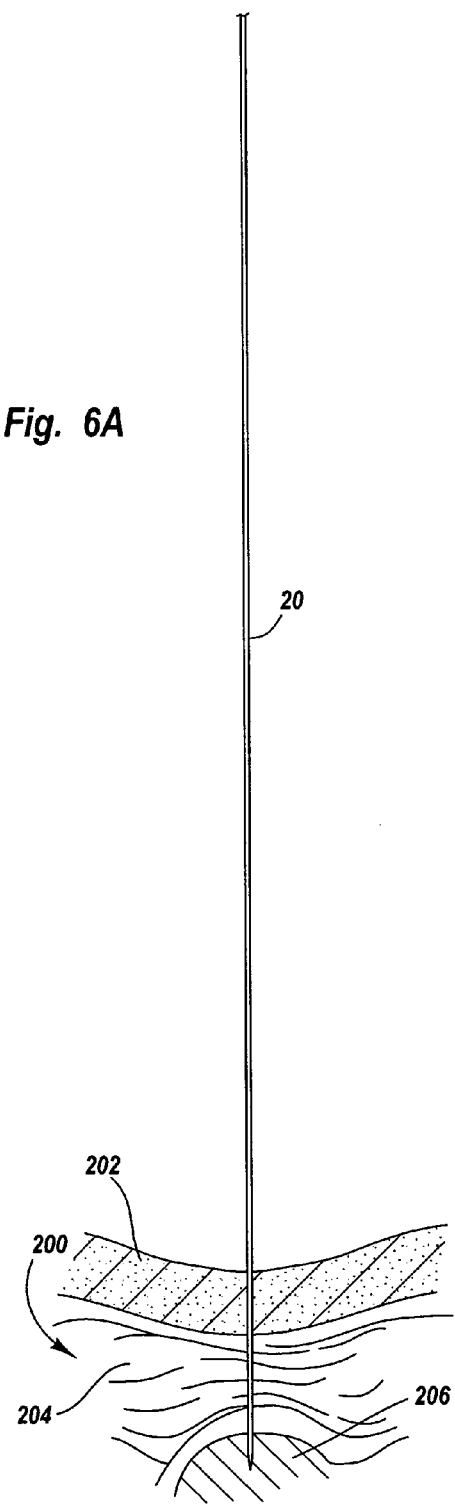
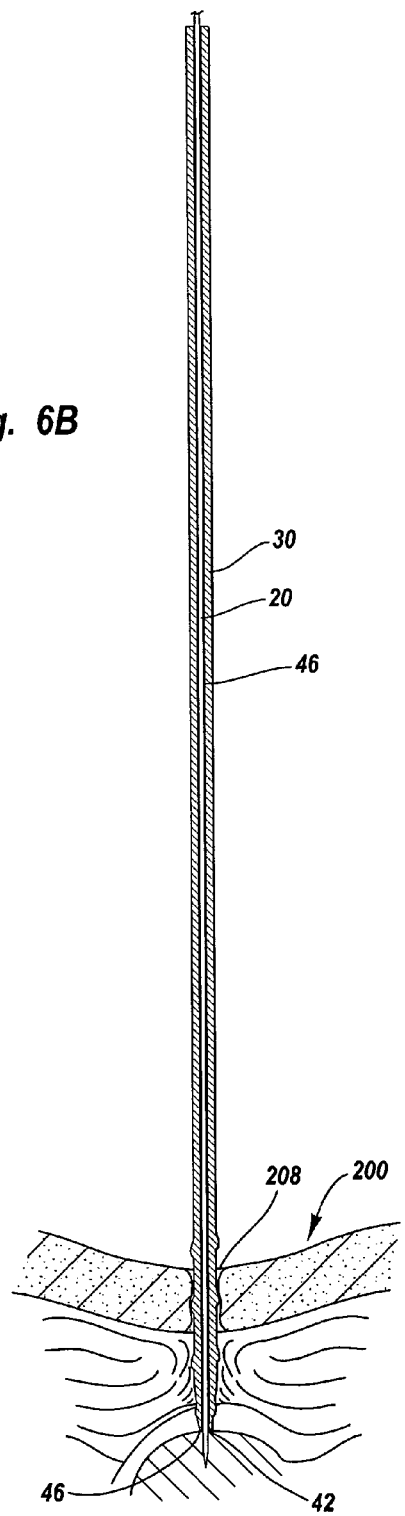
Fig. 6A
Fig. 6B

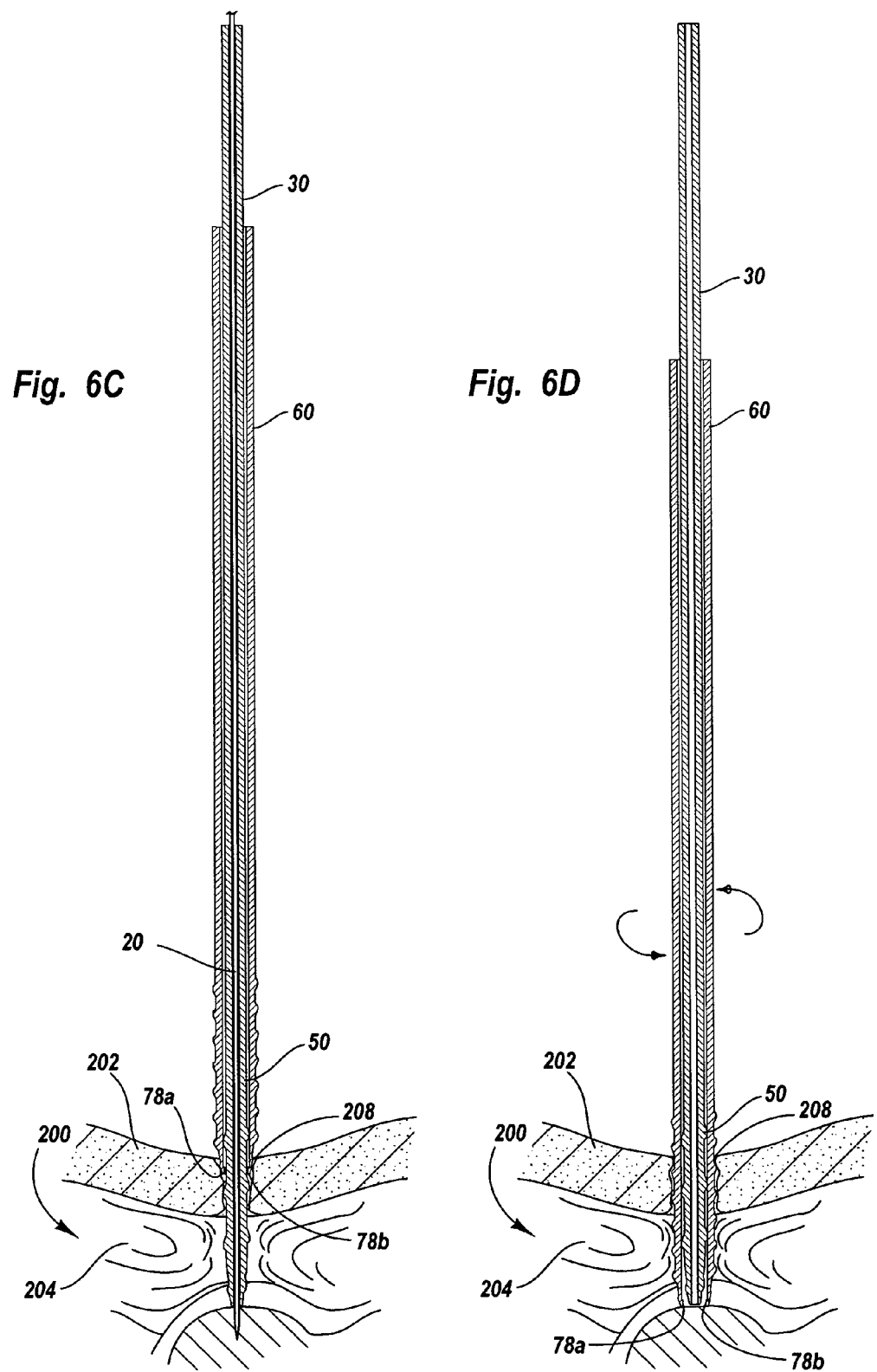

BODILY TISSUE DILATION SYSTEMS AND METHODS

CROSS-REFERENCE TO RELATED APPLICATIONS

Not applicable.

BACKGROUND OF THE INVENTION

1. The Field of the Invention

This invention is in the field of apparatus and methods for dilating bodily tissue in order to provide surgical access to a desired area of the body, such as for providing surgical access to the spine.

2. The Relevant Technology

Dilation systems are employed to move the skin, muscle, and other bodily tissues away from a surgical site in order to provide a surgeon access to bone or other bodily tissue where surgery is required. In a spinal surgery, for example, it is often desired to separate the skin and other tissue away from a particular desired surgical site prior to surgery. In order to perform this function, the skin and other tissue may be pulled away from the insertion site and a retractor placed in the insertion site to retain the skin and other tissue away from the surgical site during the surgical procedure.

One example of a dilation system that is employed during such a surgery is a dilation system having a plurality of tubular members that can be concentrically disposed. Each tubular member has a uniformly smooth interior surface and exterior surface. Initially, a guide wire is inserted within a small incision formed at the surgical site. Next, a smallest first tubular member is feed over the guide wire so that a distal end of the first tubular member is advanced into the surgical site. As the distal end advances into the incision, the tissue surrounding the first tubular member is radially outwardly retracted or dilated.

Once the first tubular member is inserted to a desired depth, a slightly larger second tubular member is pushed over the second tubular member and into the tissue so as to further dilate the tissue. This process is repeated for additionally larger tubular members until the tissue at the surgical site is retracted to a desired extent to facilitate the surgical procedure.

Although conventional dilation systems function to retract the tissue, they have a number of shortcomings. For example, it is often desirable to have each subsequent tubular member penetrate to the same depth in the tissue as the first tubular member. In conventional systems, however, it is difficult to know the exact depth that each tubular member is inserted. Furthermore, conventional tubular member are simply pushed into the tissue. Because of applied friction forces produced by the tissue, it is often difficult to advance each tubular member to a desired depth without over penetrating. That is, as static friction forces are initially overcome, the pushing force applied to a tubular member can cause the tubular member to advance too far into the tissue.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 6A is a cross-sectional schematic view demonstrating the insertion of a guide wire through the tissue of a patient into a desired surgical site.

FIG. 6B demonstrates a first dilator being placed over the guide wire of FIG. 6A and guided down to the surgical site creating an initial insertion corridor through which a surgical procedure can be performed.

FIG. 6C demonstrates the advancement of a second dilator along the first dilator such that internal mating members of the second dilator engage the external mating members of the first dilator, thereby following and enlarging the initial insertion corridor.

FIG. 6D demonstrates the second dilator having reached the surgical site, as demonstrated by the release of the internal mating members of the second dilator from the external mating members of the first dilator such that the second dilator rotates freely about the tapered portion of a first dilator.

FIGS. 7-9A are cross sectional side views of alternative embodiments of internal and external mating members that can be used on dilators.

DETAILED DESCRIPTION OF THE PREFERRED EMBODIMENTS

Figure 1:
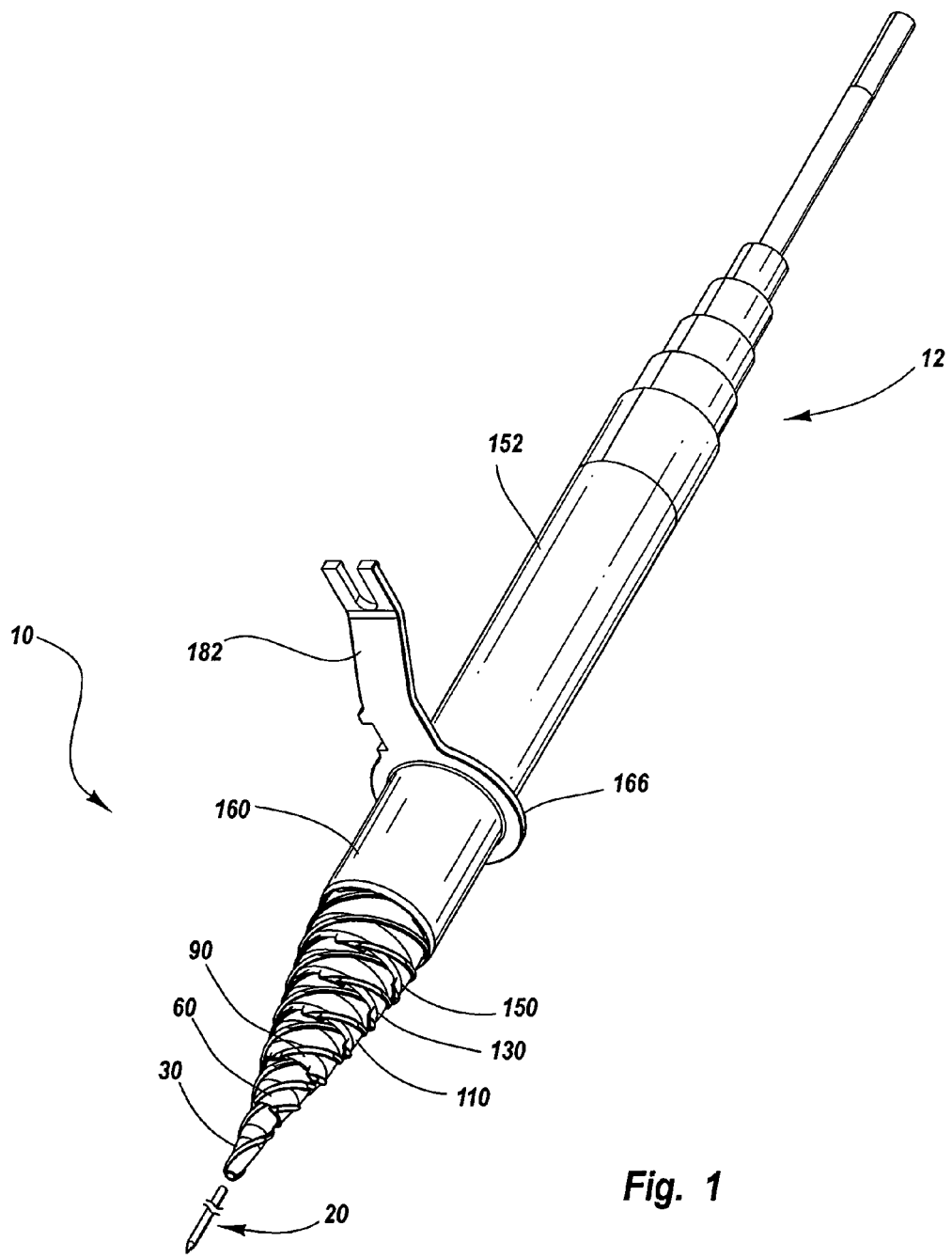
FIG. 1 is a perspective view of a dilation system of the present invention with the dilators shown in a nested, telescoping assembly.

FIG. 1 is an example of a dilation system 10 for dilating bodily tissue. System 10 comprises (i) a guide wire 20 that is inserted to a surgical site; (ii) a plurality of concentric sequentially larger dilators 30, 60, 90, 110, 130, 150 (shown as being nested in FIG. 1) that are sequentially introduced into bodily tissue over the guide wire; and (iii) a retractor 160 that is introduced over the largest introduced dilator 150.

After guide wire 20 is inserted to a desired depth within the tissue of a surgical site, first dilator 30 is passed over guide wire 20 and into the tissue. First dilator 30 circumferentially stretches or dilates the bodily tissue a certain distance, thereby forming an initial insertion corridor. The larger diameter dilators are then sequentially passed over first dilator 30 so as to further dilate the bodily tissue and form a sequentially larger insertion corridor at the surgical site.

Once the largest diameter dilator 150 has been introduced, the retractor 160 is introduced over the dilator 150, thereby establishing the final diameter of the insertion corridor and maintaining the insertion corridor during a surgical procedure. Following removal of the guide wire 20 and dilators 30-150, surgical devices and instruments can be inserted through the retractor 150 to the surgical site.

In one embodiment of the present invention, in order to avoid over-penetration of the surgical site, the dilators 30-150 and retractor 160 have complementary mating members on select interior and exterior surfaces. More specifically, dilators 30-150 feature one or more threads disposed on the exterior surface at a distal end of each dilator. One or more tangs project from the interior surface of dilators 60-150. As a larger dilator is advanced over a smaller dilator, the tang(s) engage with the thread(s) so as to force the larger dilator to travel along a fixed path relative to the smaller dilator. In one embodiment, the exterior surface at the distal end of each dilator radially inwardly tapers. The taper is configured such that the tang(s) disengage from the thread(s) when the larger dilator is inserted to the desired depth. Thus a surgeon is able to both visually see and tactilely feel when each dilator is inserted to a desired depth.

The components of the guide wire 20 and dilators 30-150 and their interaction will now be described in additional detail with reference to FIGS. 2-3A. The retractor 160 will then be described in additional detail in FIGS. 4-5 and a method for dilating tissue using system 10 will then be described with reference to FIGS. 6-6L. Additional alternative embodiments will then be discussed with reference to FIGS. 7-10.

Figure 2:
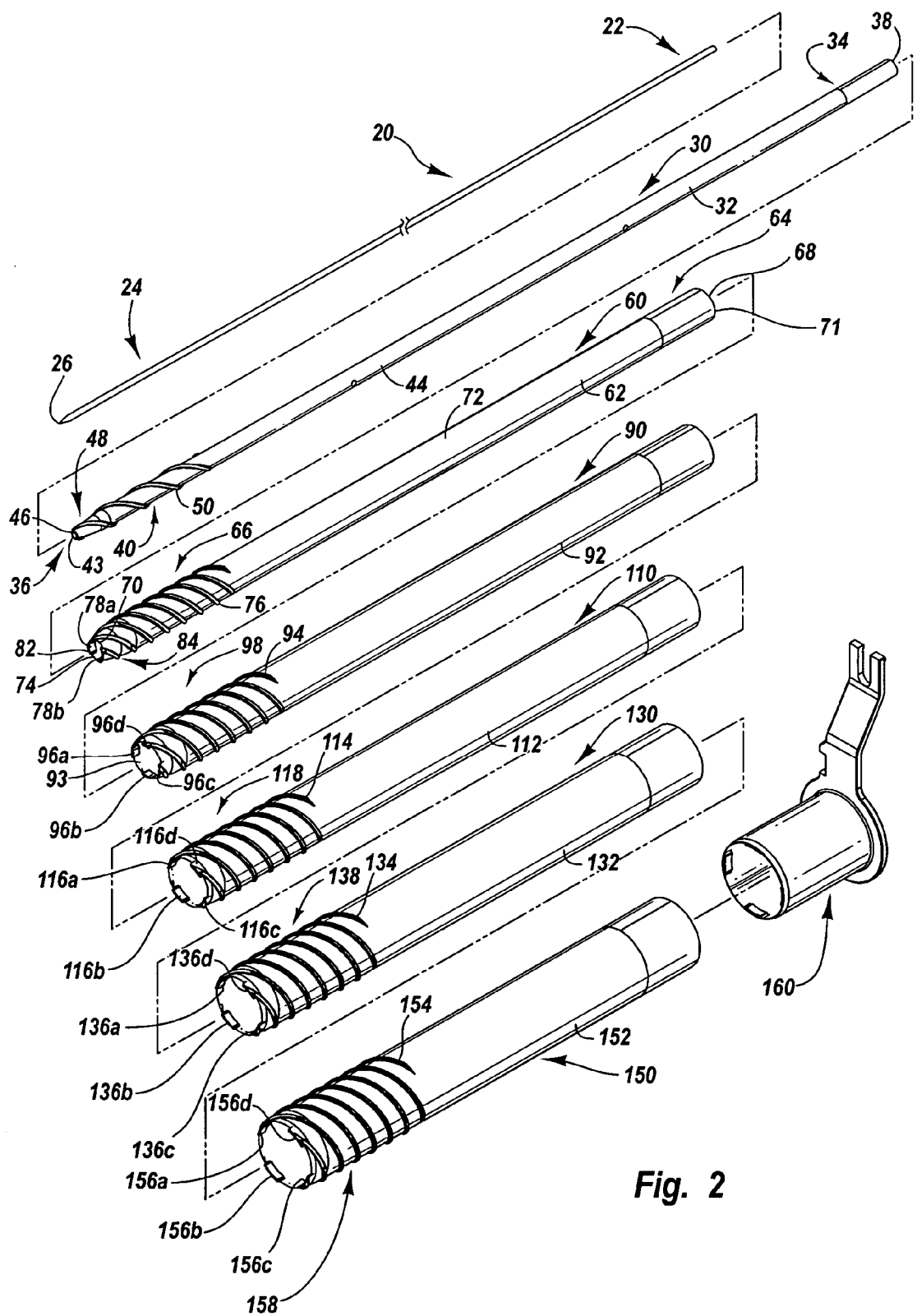
FIG. 2 is an exploded view of the dilation system of FIG. 1 with the broken lines demonstrating the sequential advancement of a dilator of the system along a guide wire, followed by larger dilators being advanced sequentially along the initial dilator and each other, followed by a tubular retractor being advanced along the largest dilator of the system.
Figure 3:
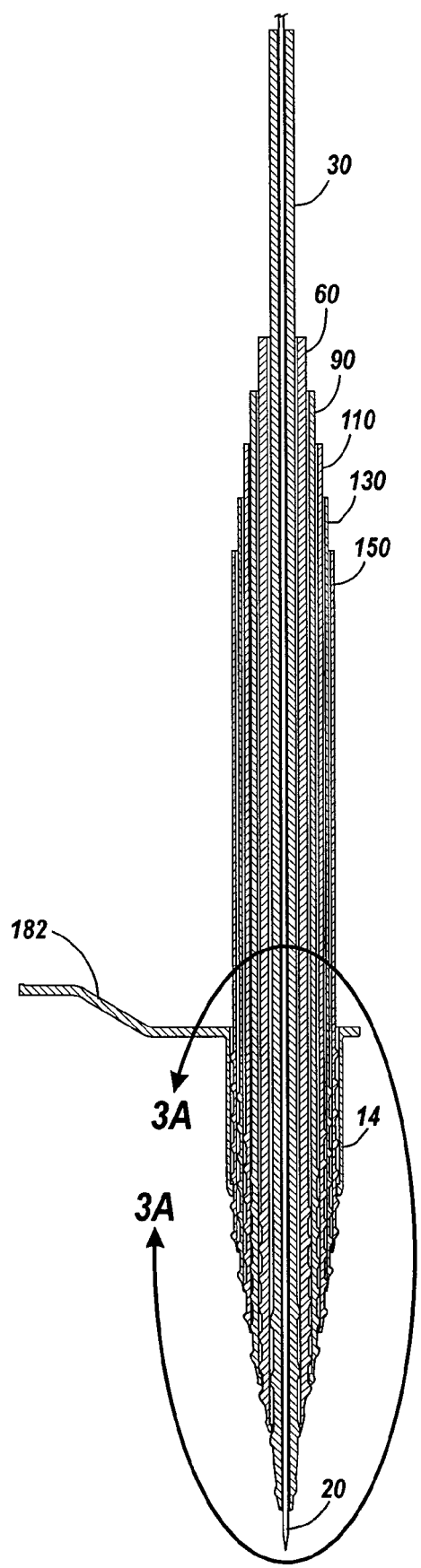
FIG. 3 is a cross sectional view of the dilation system of FIG. 1.
Figure 3A:
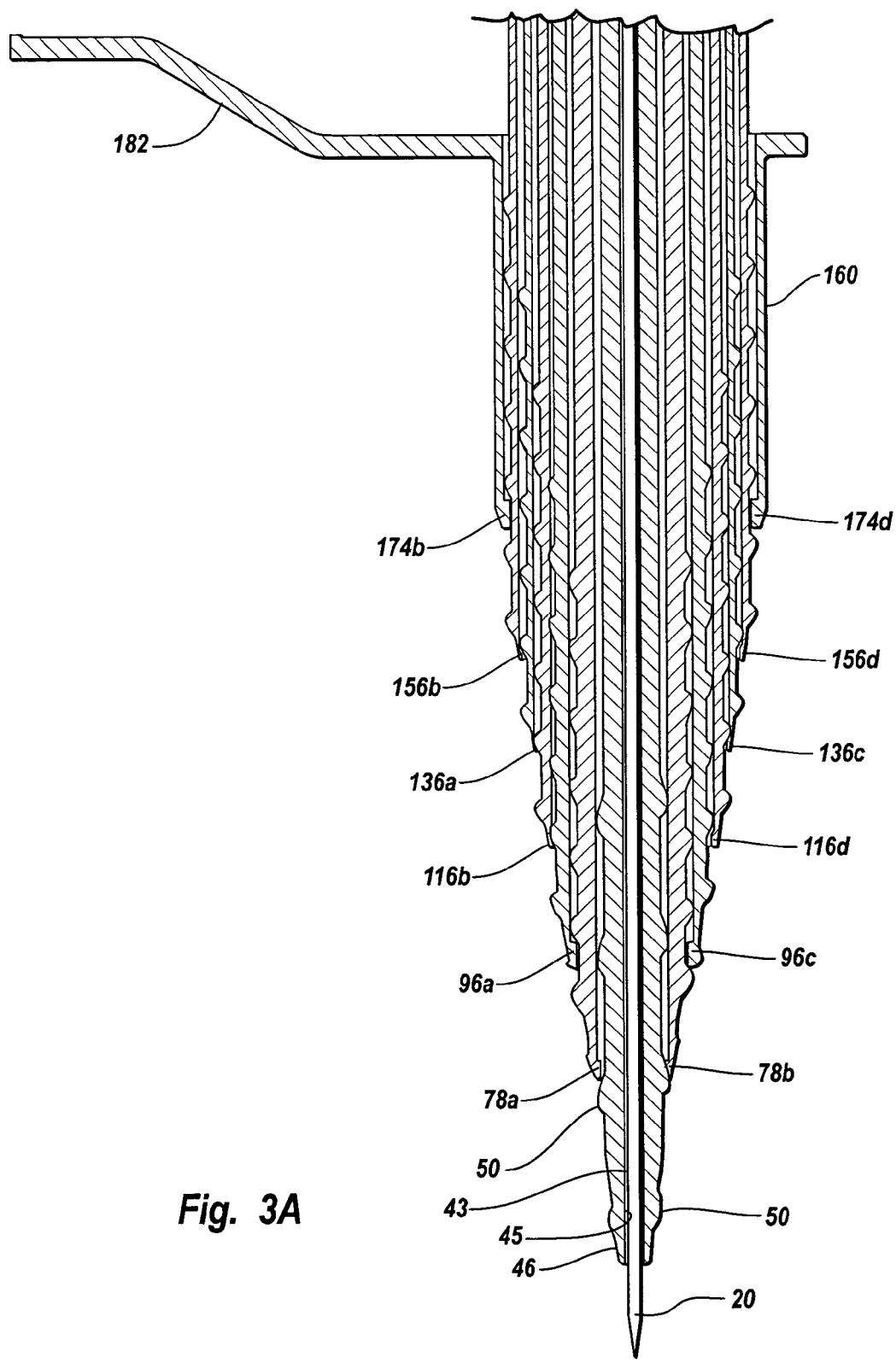
FIG. 3a is an enlarged view of the distal insertion ends of the dilators shown in FIG. 3.

With reference now to FIGS. 2-3a, guide wire 20 has a proximal end 22 and a distal insertion end 24 that terminates at a distal tip 26. Guide wire 20 can comprise any conventional guide wire. Once guide wire 20 is inserted into a desire surgical site on the body, first dilator 30 is received over proximal end 22 of guide wire 20 and advanced along guide wire 20.

Dilator 30 comprises an elongated tubular body 32 having an exterior surface 44 and an interior surface 45 each extending between a proximal end 34 and an opposing distal insertion end 36. Interior surface 45 bounds a passageway 43 having a proximal opening 38 at the proximal end 34 and a distal opening 40 at the distal end 36. Passageway 46 is configured to allow guide wire 20 to pass therethrough. The exterior surface 44 includes a tapering portion 48 that constricts towards and terminates at a distal terminus 46. In other words, the distal insertion end 36 of tubular body 32 has a tapering portion 48 that decreases in diameter toward distal terminus 46. Tapering portion has a substantially frustoconical configuration. Dilator 30, as with the other dilators, can be made of any material such as metal, plastic, or composite and can be radiopaque or radiolucent.

Dilator 30 further comprises an external mating member outwardly projecting from exterior surface 44 of tubular body 32 at distal insertion end 36. In the embodiment depicted, the external mating member comprises an external thread 50 helically extending around tubular body 32 on exterior surface 44. Thread 50 is formed on tapering portion 48 and extends to distal terminus 46. In one alternative, thread 50 can comprise two or more discrete threads.

Similar to first dilator 30, second dilator 60 comprises an elongated tubular body 62 having an exterior surface 72 and an interior surface 74 each extending between a proximal end 64 and an opposing distal insertion end 66. Interior surface 74 bounds a passageway 71 having a proximal opening 68 at the proximal end 64 and a distal opening 70 at the distal insertion end 66. Passageway 71 of second dilator 60 is configured to receive first dilator 30. Second dilator 60 also has a tapering portion 84 located at distal insertion end 66 that decreases in diameter toward and terminates at a distal terminus 82.

As further shown, second dilator 60 has an external mating member outwardly projecting from exterior surface 72 and an internal mating member projecting from interior surface 74 of tubular body 62 each at distal insertion end 66. Specifically, the external mating member comprises one or more threads 76 formed on exterior surface 72 and the internal mating member comprises first and second tangs 78a-b projecting on the interior surface 74 at or adjacent to distal terminus 82.

Tangs 78a-b of second dilator 60 are configured to threadedly mate with thread 50 of first dilator 30 when second dilator 60 is advanced over first dilator 30, as shown in FIGS. 3 and 3A. In this regard, thread 50 forms bounded tracks that receive and guide tangs 78a-b. Specifically, once proximal end 34 of first dilator 30 is received within distal insertion end 66 of second dilator 60, second dilator 60 can be freely advanced over first dilator 30 until tangs 78a-b reach thread 50. Further advancement of second dilator 60 requires selective rotation of second dilator 60 relative to first dilator so that tangs 78a-b engage with and advance along thread 50. During the engagement between tangs 78a-b and thread 50, second dilator 60 is forced to travel along a fixed path that prevents free rotation of second dilator 60 relative to first dilator 30. That is, second dilator 60 can only rotate along the fixed path. It is noted that second dilator 60 has a length that is shorter than first dilator 30. This variance in length enables first dilator 30 to be held stationary by the surgeon holding onto the exposed proximal end 34 of first dilator 30 while second dilator 30 is advanced and rotated.

As tangs 78a-b are threaded downwardly along external thread 50, the tangs 78a-b reach the tapered portion 48 of first dilator 30. Tapered portion 48 is configured such that at the point when distal terminus 82 of second dilator 60 is aligned with distal terminus 46 of first dilator 30, tangs 78a-b disengage from thread 50 due to the constriction of tapered portion 48. As a result of tangs 78a-b disengaging from thread 50, second dilator 60 is again free to rotate relative to first dilator 30. Upon feeling the free rotation, the surgeon knows that the second dilator 60 is at the same depth as first dilator 30 and thus can stop further advancement into the tissue, thereby preventing over-penetration of second dilator 60. In other embodiments, tangs 78a-b and thread 50 can be set so that second dilator 60 disengages from first dilator 30 at any desired relative position relative to first dilator 30.

Once dilator 60 has been inserted to the desired position, additional dilators can be added. Dilators 90, 110, 130, and 150 similarly sequentially increase in diameter and decrease in length. Each of the dilators also has an external mating member, i.e., one or more outwardly projecting threads, and an internal mating member, i.e., one or more inwardly projecting tangs. Each of the dilators also includes a tapering portion on which the external threads extend. In view of the increasing diameter size of the dilators, an increasingly larger dilator insertion corridor is formed by sequentially passing larger dilators over smaller dilators.

For example, third dilator 90 comprises a third tubular body 92 that bounds a passageway 93. Third tubular body 92 has a diameter that is larger than the diameter of second tubular body 62. An external thread 94 and interior tangs 96a-d are formed at a distal insertion end 98 of third tubular body 92. Similarly, the fourth, fifth and sixth dilators 110, 130, 150 have respective tubular bodies 112, 132, 152 each bounding a passageway extending between a proximal end and an opposing distal insertion end 118, 138, and 158, respectively. External threads 114, 134, 154 and internal tangs 116a-d, 136a-d, 156a-d are formed on distal insertion ends 118, 138, and 158 of dilators 110, 130, 150, respectively.

As indicated, each of the sequentially larger dilators 110, 130, 150 also has a tapered distal portion at the distal insertion end thereof. As a result, the internal mating members of each larger dilator are configured to engage with external mating members of the next smaller dilator received therein. The larger dilator disengages from the smaller dilator when the distal terminus of the larger dilator aligns with the distal terminus of the smaller dilator.

In addition, the tubular retractor 160, as will be discussed below in greater detail, is designed to spin freely about the final dilator 150 when the retractor 160 is placed thereabout and threaded along the distal insertion end 158 thereof.

FIGS. 3 and 3A show a nested mating relationship of the dilators 30-150, with the dilator 30 over the guide wire 20 and with the retractor 160 being shown over the dilator 150. As shown in these views, the internal tangs 78a and 78b can be threaded along exterior thread 50 of dilator 30 and the internal tangs of the subsequently larger dilators can mate with exterior threads of respective dilators.

FIGS. 3 and 3A illustrate the interlocking features of the various dilators and their possible relationship with respect to each other. FIGS. 1, 3 and 3A also illustrate how the guide wire 20, dilators 30-150, and retractor 160 can be conveniently stored prior to use, for example. During a surgical procedure, once dilator 30 is placed over guide wire 20, guide wire 20 may be removed or retained as other dilators are applied. Similarly, dilator 30 may be removed or retained from within dilator 60 once dilator 60 is passed over dilator 30, as can the other dilators once the larger dilators are passed over them.

Retractor 160 will now be described in additional detail with reference to FIGS. 2-5. Retractor 160 comprises a tubular body 161 having a proximal end 162 and an opposing distal insertion end 164. A proximal opening 166 is formed at the proximal end 162 and a distal opening 168 is formed at the distal end 164. Body 161 also has an exterior surface 170 and an interior surface 172, each extending from the proximal end 162 to the distal insertion end 164. As shown, mounted on the interior surface at the distal insertion end 164 thereof are a plurality of internal mating members. Specifically, tangs 174a-d are formed on interior surface 172 so as to mate with the external thread 154 of the last dilator 150. As with other dilators, tangs 174a-d of retractor 160 are designed to disengage from thread 154 when the distal terminus 175 of retractor 160 is aligned with the distal terminus of dilator 150.

Figure 4:
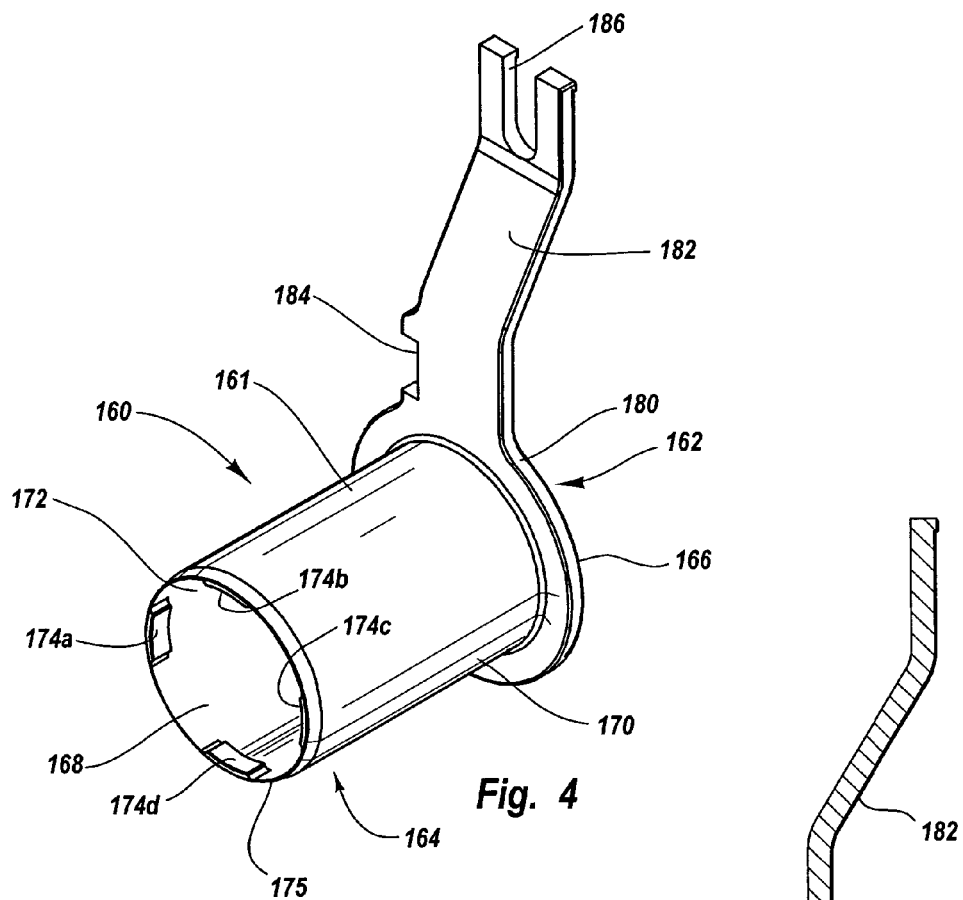
FIG. 4 is a perspective view of the tubular retractor of the dilation system of FIGS. 1 and 2.
Figure 5:
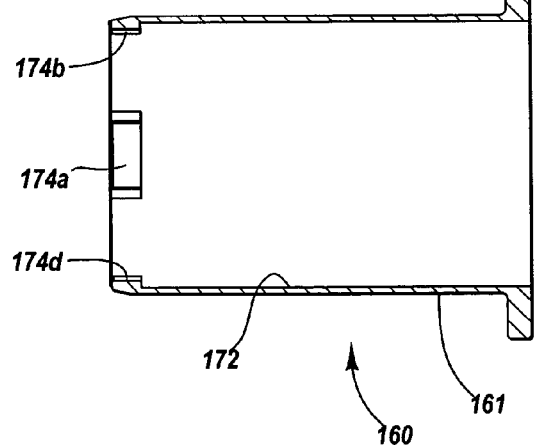
FIG. 5 is a cross-sectional view of the retractor of FIGS. 1, 2 and 4.

Retractor 160 is also shown in FIG. 5 in a cross-sectional view. As shown in FIGS. 4 and 5, tangs 174a-d comprise a small tab or other form of projection that extends inwardly from the interior surface 172 of tubular body 161 so as to engage the thread on dilator 150. Optionally, the mating member or members may comprise one or more threads. In yet other embodiments, retractor 160 can be free of mating members on its interior surface. In this embodiment, retractor 160 does not mechanically engage with dilator 150.

Extending about tubular body 161 is an annular rim 180. Rim 180 has a connecting arm 182 extending therefrom. The connecting arm 182 has an intermediate notch 184 and a peripheral notch 186. A surgical instrument, e.g., equipment, tools, or supplies, may be coupled to the connecting arm 182 for use during surgery or may be coupled to the connecting arm 182 in order to stabilize the retractor and prevent it from moving during the surgery. The notches are configured to receive or otherwise couple to such instruments. For example, in one embodiment a stabilizing arm is connected to one or more notches in order to stabilize the retractor 160 in a desired position during a surgical procedure. The rim 180 may rest on the skin surrounding the periphery of the insertion corridor during surgery, for example. Arm 182 is thus linked to the tubular body 161 of the retractor. The arm 182 may be linked to the tubular body 161 by being indirectly coupled thereto or by being coupled directly thereto.

Figure 6E:
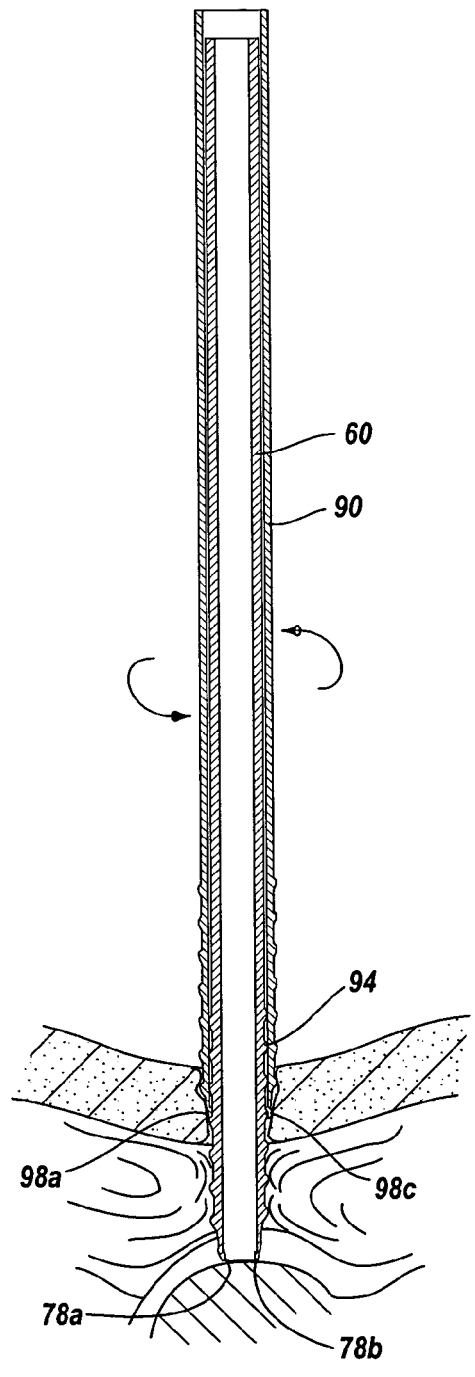
FIG. 6E demonstrates the advancement of a third dilator over the second dilator after the first dilator has been removed from within the second dilator.

With reference now to FIGS. 6a-6k, a method for dilating bodily tissue will now be discussed. As shown in FIG. 6a, in one embodiment a guide wire 20 is first passed through bodily tissue 200 such as skin 202 and muscle 204 until a portion of bone 206, e.g., a vertebrae, or another surgical site is contacted. In another embodiment, the guide wire 20 is passed through bodily tissue without contacting bone. The guide wire 20 may be inserted through a small incision, e.g., a 10-15 mm incision.

Next, as shown in FIG. 6b, first dilator 30 is advanced over guide wire 20 and into the tissue until the distal terminus 46 of first dilator 30 contacts the surgical site. The external thread 50 of dilator 30 may be used in a cutting or corkscrew fashion to dilate the bodily tissue by rotating dilator 30 as dilator 30 is advanced into the insertion corridor along guide wire 20. External thread 50 thus helps to control the advancement of dilator 30 into the tissue as dilator is rotated. As shown, upon advancing the first dilator over the guide wire 20 a desired distance, the tissue 200 begins to separate, forming an insertion corridor 208 in the bodily tissue 200. As will be illustrated in the next figures, the insertion corridor 208 increases as the diameter of the dilator therein increases.

Once the distal insertion end 36 of the first dilator 30 is advanced to a desired location, the guide wire 20 can then be removed from within the first dilator 30. Optionally, the guide wire 20 can be allowed to remain within first dilator 30 and can be removed once the retractor 160 has been placed within the insertion corridor 208. As another option, it is possible to insert first dilator 30 into bodily tissue and begin formation of an insertion corridor without initially employing a guide wire to begin the insertion corridor.

FIG. 6C demonstrates the placement of second dilator 60 over first dilator 30. The Figure illustrates that the internal tangs 78a-b of second dilator 60 engage the thread of first dilator 30 so as to thereby selectively thread downwardly into the insertion corridor 208 formed by first dilator 30. Once the sequentially larger diameter dilator (e.g., dilator 60) is passed over the smaller diameter dilator (e.g., dilator 30), the surgeon can hold the smaller diameter dilator 30 in place by grasping the exposed proximal end of the dilator 30.

As shown in FIG. 6D, once tangs 78a-b of second dilator 60 are moved adjacent the tapering portion 48 of first dilator 30, tangs 78a-b disengage from thread 50 on the exterior surface of dilator 30. This enables tangs 78a-b and thus second dilator 60 to freely rotate in either direction with respect to first dilator 30. As previously mentioned, tangs 78a-b disengage from thread 50 when the distal terminus of second dilator 60 is aligned with the distal terminus of first dilator 30. Accordingly, the ability to freely rotate the second dilator 60 relative to the first dilator 30 signals to the practitioner that the surgical site has been reached, as shown in FIG. 6D. The practitioner can then stop advancing the second dilator 60 and thus prevent over-penetration of the second dilator 60 into the surgical site. Once second dilator 60 has reached the surgical site of FIG. 6D, the first dilator 30 can then be removed from within the second dilator 60 or be allowed to remain therein. Also as shown in FIG. 6D, the distal insertion end of the second dilator 60 is disengaged from, but continues to surround the distal insertion end of the first dilator 30.

Figure 6F:
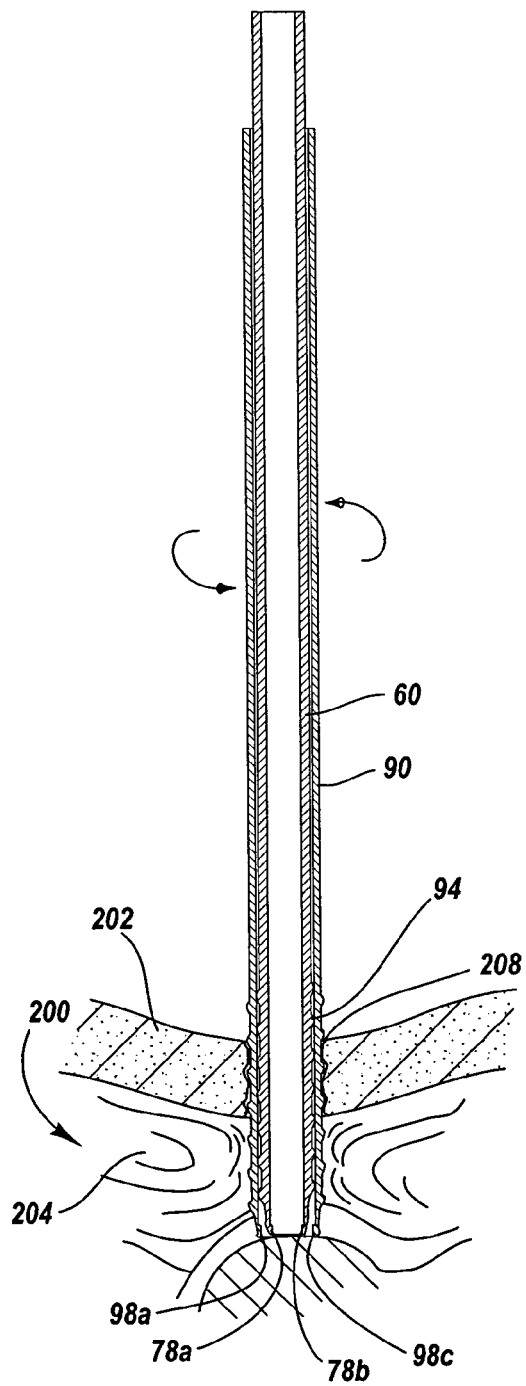
FIG. 6F demonstrates the third dilator having reached the surgical site.

FIGS. 6E-6I demonstrate the placement of subsequently larger dilators 90-150 into insertion corridor 208 by threading dilator 90 over dilator 60 and threading subsequently larger dilators over dilator 90. The progressively larger dilators are threaded over the previous dilator until the insertion corridor is dilated to the desired diameter. FIG. 6E demonstrates the advancement of third dilator 90 along the thread 76 of second dilator 60. FIG. 6F demonstrates that third dilator 90 has reached the surgical site, has dilated the insertion corridor 208 and can freely rotate with respect to second dilator 60.

Figure 6G:
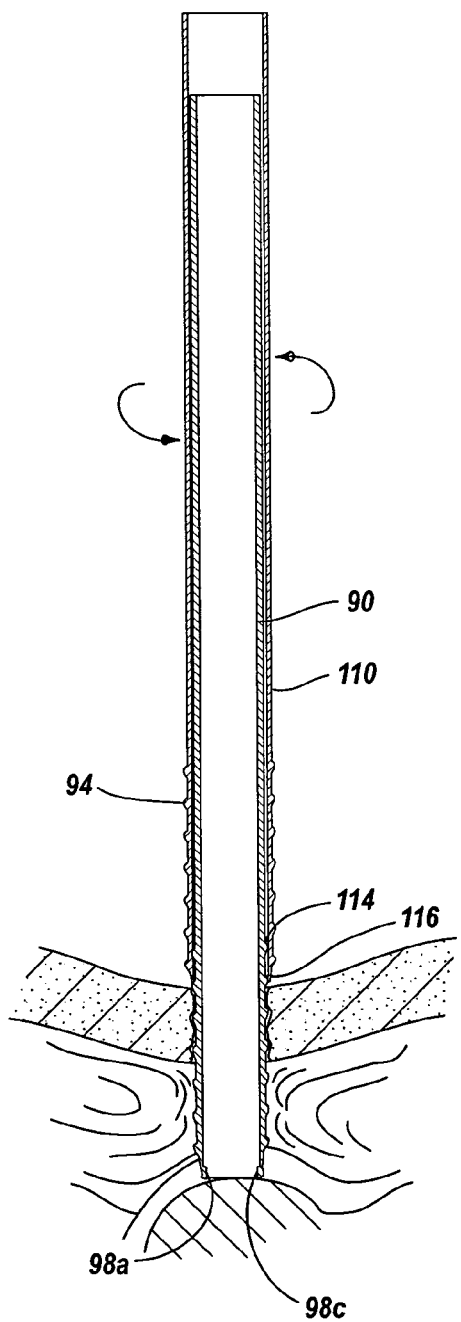
FIG. 6G demonstrates the advancement of a fourth dilator over the third dilator after the second dilator has been removed from within the third dilator.
Figure 6H:
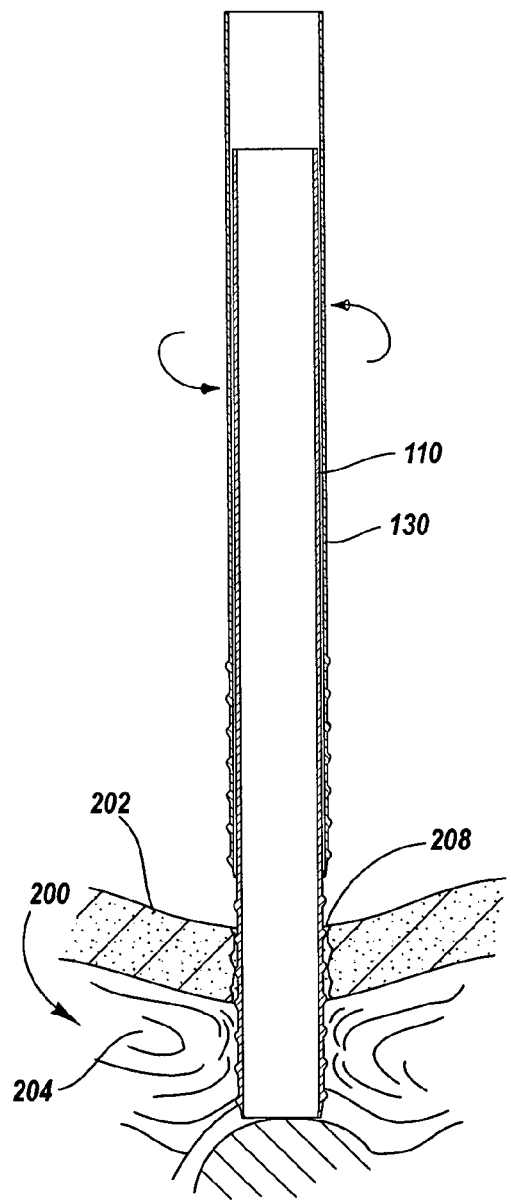
FIG. 6H demonstrates the advancement of a fifth dilator over the fourth dilator after the third dilator has been removed from within the fourth dilator.
Figures 6I, 6J:
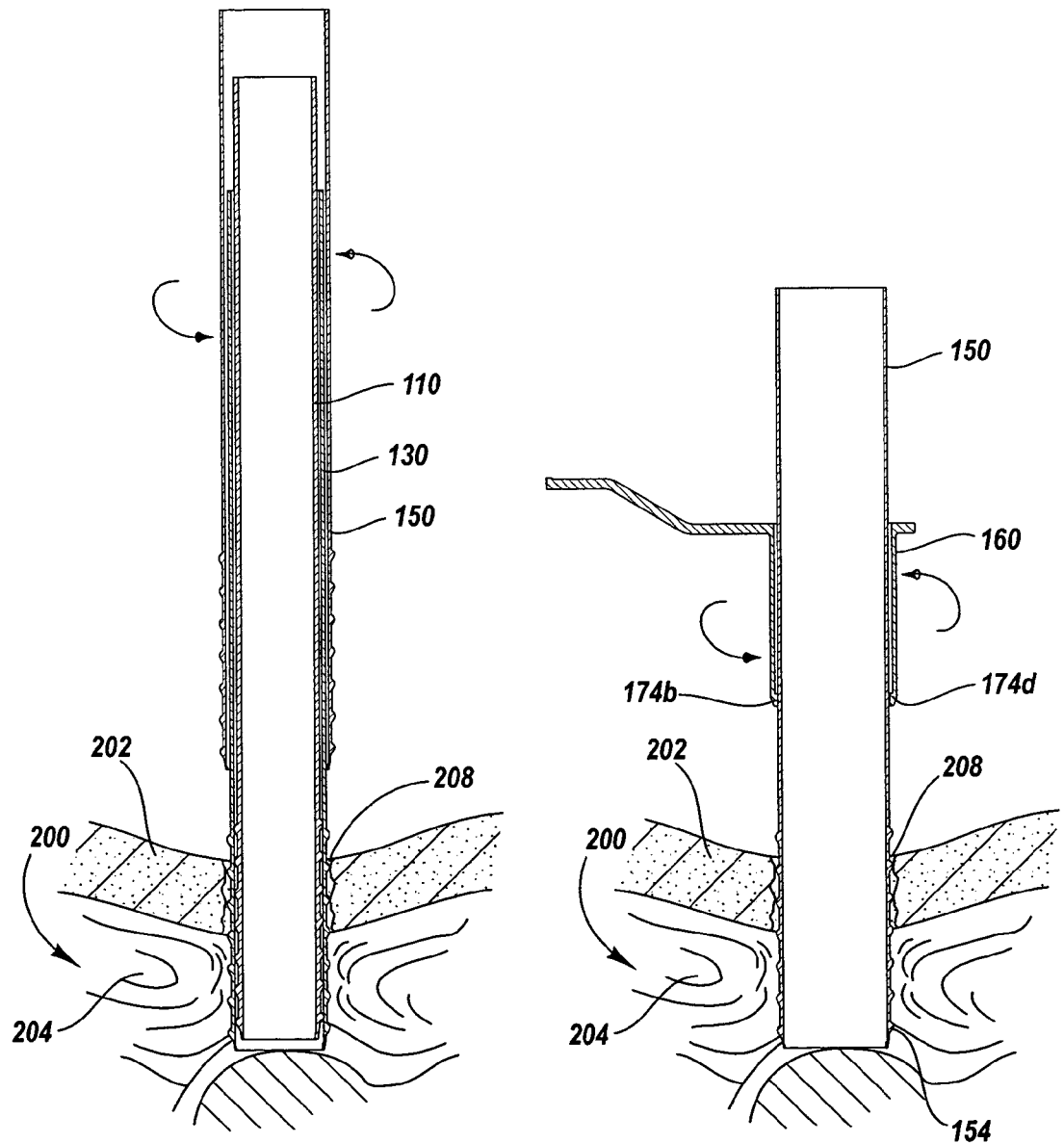
FIG. 6I demonstrates the advancement of a sixth dilator over the fifth dilator while the fourth dilator remains within the fifth dilator.
FIG. 6J demonstrates the advancement of a tubular retractor over the sixth dilator.

FIG. 6G demonstrates the placement of fourth dilator 110 over third dilator 90 (following the removal of dilator 60 from within dilator 90). FIG. 6H demonstrates the placement of fifth dilator 130 over fourth dilator 110 (following the removal of third dilator 90 from within fourth dilator 110). FIG. 6I demonstrates the placement of the sequentially largest sixth dilator 150 over fifth dilator 130 while fourth dilator 110 is still located within fifth dilator 130—illustrating that the subsequently larger dilator may optionally be placed over a dilator while another smaller dilator is still therein.

Figure 6K:
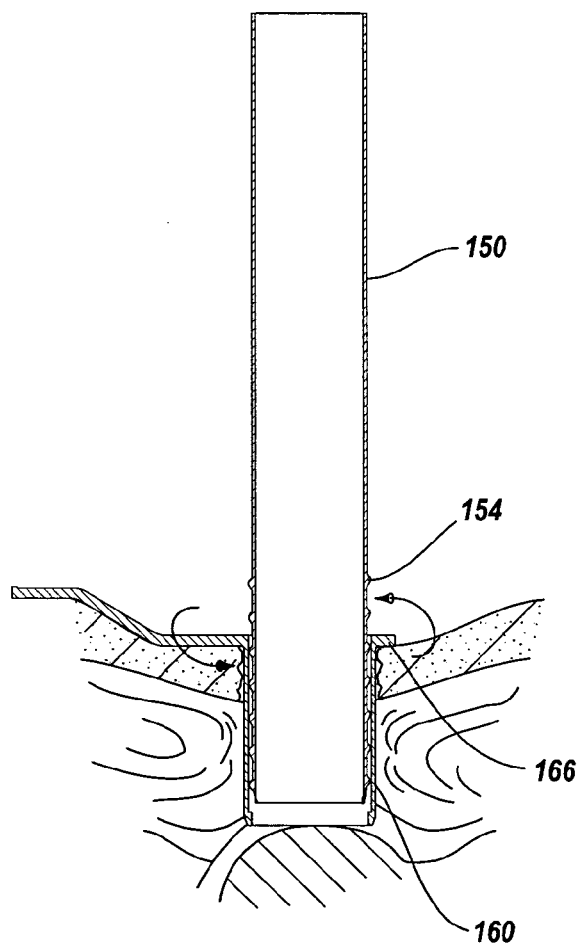
FIG. 6K demonstrates the retractor having reached the surgical site, as demonstrated by the release of the internal mating members of the retractor from the external mating members of the sixth dilator such that the retractor rotates freely about the tapered portion of a sixth dilator.
Figure 6L:
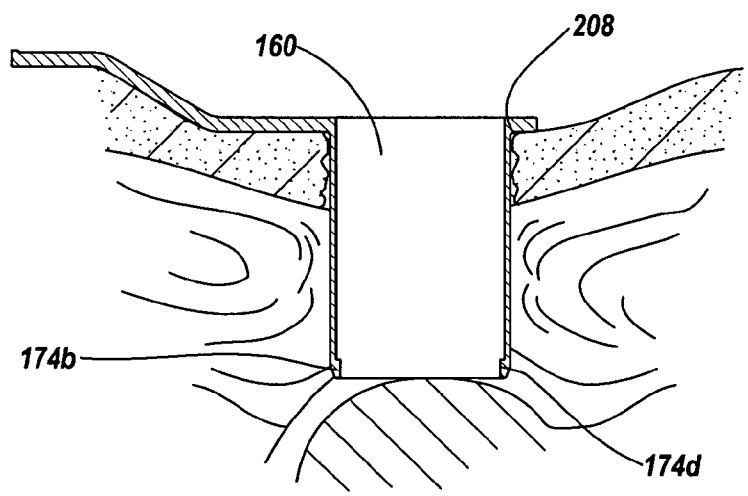
FIG. 6L demonstrates the retractor having reached the surgical site and the sixth dilator having been removed therefrom such that a surgical instrument can be advanced through the retractor.

FIG. 6J demonstrates the placement of retractor 160 over dilator 150. FIG. 6K illustrates the movement of retractor 160 to the surgical site, threading over dilator 150. Once all the dilators, including dilator 150 have been removed, tubular retractor 160 remains in the surgical site, retracting the bodily tissue and retaining the insertion corridor 208 during a surgical procedure.

As reflected in FIG. 2 and previously mentioned, as the diameters of the sequential dilators 30, 60, 90, 110, 130, 150 increase, the lengths of the sequential dilators decrease. Thus, first dilator 30 is longer than second dilator 60, which is longer than third dilator 90, and so on. The decreasing length of the sequentially increasing diameter dilators enables the smaller diameter dilators to be held in position while a larger diameter dilator is advanced thereover. It also enables a smaller diameter dilator to be removed while a larger diameter dilator is held in place.

In order for the larger diameter dilator to freely rotate with respect to the smaller diameter dilator, the interior mating members must be short enough that they do not engage the exterior thread of the smaller dilator when moved adjacent a tapered portion. The tangs disclosed in FIGS. 2-5, for example, are sufficiently short that they can engage the exterior thread until reaching the tapered portion wherein the tangs disengage from the threads. In contrast or conjunction to tapering the bodies of the dilators, the distal ends of the threads can taper toward the distal end or can terminate prior to the distal terminus of the dilators. In either embodiment, the tangs can disengage from the threads when the distal terminus are aligned.

In one embodiment of the present invention, means are provided for forcing a second dilator to travel along a substantially fixed path that prevents free rotation of second dilator relative to a first dilator while at least a portion of the second dilator is being advanced over the first dilator. By way of example and not by limitation, one embodiment of the recited means corresponds to the external threads, such as threads 50, 76, and 94, and the corresponding internal tangs which engage with the external threads, such as tangs 78, 96, and 116, as described above. It is appreciated, however, that there are a variety of alternative embodiments which can be used to accomplish the same function. For example, any number of complementary tangs and threads can be used in a given embodiment. Furthermore, the tangs can be replaced with any form of projection that engages with the threads. In yet another embodiment, the tangs and threads need not be located at the distal insertion end of the first and second dilator. Rather, the tangs and threads can be located at any complementary location along the dilators. For example, if the threads and tangs are disposed along a central section of the dilators, the tangs can be positioned to disengage from, i.e., move distally past, the threads at the point where the distal terminus of the second dilator is aligned with the distal terminus of the first dilator. In this embodiment the threads need not be on a tapered portion.

Figure 7:
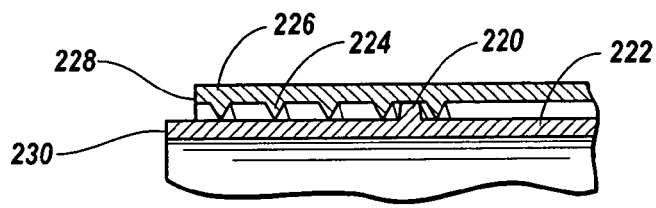

In yet another embodiment, the tangs and threads can be reversed. For example, as depicted in FIG. 7, a tang 220 is mounted on an exterior surface of an inner dilator 222 while a thread 224 is helically formed on an interior surface of an outer dilator 226. Again, tang 220 is positioned relative to thread 224 such that when a distal terminus 228 of outer dilator 226 is aligned with a distal terminus 230 of inner dilator 222, tang 220 disengages from thread 224 so that outer dilator 226 can freely rotate about inner dilator 222.

Figure 8:
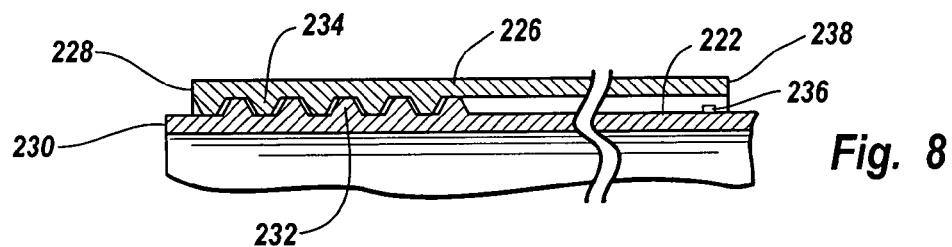

In still another embodiment as depicted in FIG. 8, one or more threads 232 can be formed on the exterior surface of inner dilator 222 while one or more complementary threads 234 can be formed on the interior surface of outer dilator 226. The engagement between threads 232 and 234 causes outer dilator 226 to move in a fixed path relative to inner dilator 222. In the embodiment depicted, outer dilator 226 cannot freely rotate relative to inner dilator 222 when distal terminuses 228 and 230 are aligned due to the continued engagement between threads 232 and 234. Although not required, in the depicted embodiment a marking 238 is formed on the exterior surface of inner dilator 222. Marking 238 is positioned to align with a proximal terminus 238 of outer dilator 226 when distal terminuses 228 and 230 are aligned. This again helps the surgeon ensure that outer dilator 226 does not over-penetrate the surgical site. It is also appreciated that by forming the threads 232 and 234 proximal, the threads can be aligned to disengage when distal terminuses 228 and 230 are aligned. It is further appreciated that the threads and other various mating members can be formed along the entire length of one or both of the dilators.

Figure 9A:
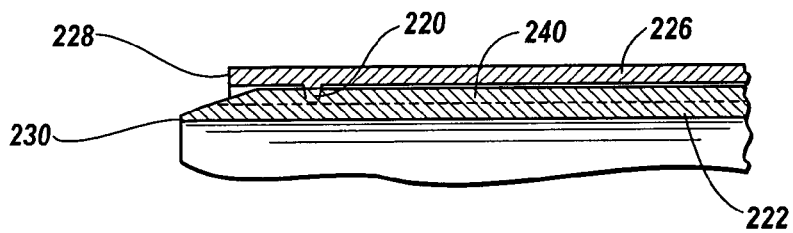
Figure 9B:
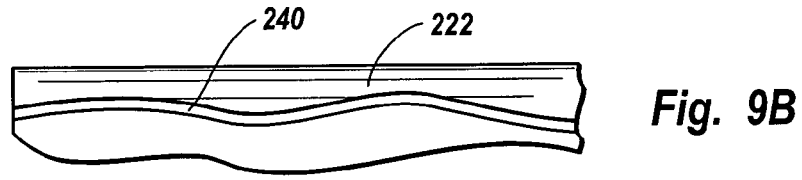
FIGS. 9B-9D are elevated side views of the exterior surface of the inner dilator shown in FIG. 9A having different track configurations that function as mating members.
Figure 9C:
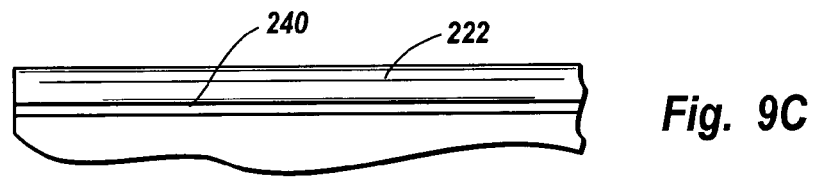
Figure 9D:
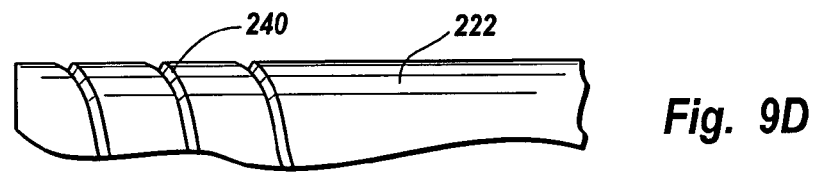

In yet another embodiment as depicted in FIG. 9A, a mating member comprises a track 240 formed along the exterior surface of inner dilator 222. Tang 220 projects from the interior surface of outer dilator 226 and is configured to be received within track 240. As a result, outer dilator 226 is forced to travel along a fixed path relative to inner dilator 222. Track 240 can be any desired configuration. For example, in FIG. 9B track 240 has a sinusoidal configuration while in FIG. 9C track 240 is linear. In FIG. 9D, track 240 is helical. Although not required, depicted in FIG. 9A track 240 ends at a tapered section such that tang 220 disengages from track 240 when distal terminus 228 and 230 are aligned. Outer dilator 226 is thus free to rotate relative inner dilator 222.

In still other embodiments it is again appreciated that track 240 and tang 220 can be switched between the interior and exterior surfaces. Various tracks can also be formed by outwardly projecting threads, as in FIG. 7, or by rails or other projecting members. In view of the foregoing, it is appreciated that there is a wide variety of different type, configures, size and numbers of mating members that can be used to complementary mate so that a second dilator is caused to travel along a substantially fixed path that prevents free rotation of second dilator relative to a first dilator while at least a portion of the second dilator is being advanced over the first dilator.

Although FIGS. 7-9 only show mating members on the interior surface of outer dilator 226 and the exterior surface of inner dilator 222, it is also appreciated that mating members can be formed on the exterior surface of outer dilator 226 and the interior surface of inner dilator 222 so as to further mate with other dilators or retractors.

Figure 10:
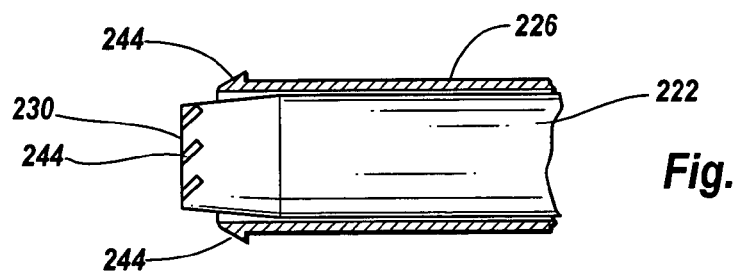
FIG. 10 is a partial cross sectional side view of an inner and outer dilator having tissue engaging members formed thereon.

The present invention also provides tissue engaging members. The tissue engaging members enable smooth and controlled advancement of the dilators into the body tissue. For example, depicted in FIG. 10 is inner dilator 222 having sloped thread portions 244 formed on the exterior surface adjacent to distal terminus 230. Thread portions 244 function like a drill bit or auger to help advance inner dilator 222 in a controlled manner into the body tissue as second dilator 222 is selectively rotated. This controlled advancement helps to eliminate over-penetration caused by pushing on conventional dilators. In like manner, thread portions 244 are also formed on the exterior surface of outer dilator 226. In alternative embodiments the tissue engaging members can comprise helical threads, blades, or any other type of protrusion of groove that assists the dilator in controlled advancement into the bodily tissue as the dilator is rotated.

Although tissue engaging members can have the same configuration as mating members, thread portions 244 are not referenced in FIG. 10 as a mating member because there is no complementary mating member on the interior surface of outer dilator 226 for thread portions 244 to engage. In another embodiment, separate mating members can be formed on dilators 222 and 226 proximal of thread portions 244. In yet other embodiments a structural feature may function as both a mating member and a tissue engaging member. For example, threads 50, 76, 94 in FIG. 2 function as both a mating member and a tissue engaging member.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dilation system for dilating bodily tissue, the dilation system comprising:
    an elongate first dilator comprising a tubular body having an exterior surface extending between a proximal end and an opposing distal insertion end, the body also having an interior surface bounding a passageway extending between the proximal end and the distal insertion end;
    a first mating member formed on the exterior surface of the first dilator at the distal insertion end; and
    an elongate second dilator comprising a tubular body having an exterior surface extending between a proximal end and an opposing distal insertion end, the body also having an interior surface bounding a passageway extending between the proximal end and the distal insertion end, the passageway of the second dilator being configured to receive the tubular body of the first dilator, the second dilator mechanically engaging with the first mating member such that the second dilator is forced to travel along a fixed path that prevents free rotation of the second dilator relative to the first dilator while at least a portion of the second dilator is being advanced over the first dilator, wherein the distal insertion end of the first dilator and the second dilator each terminate at a distal terminus, the second dilator mechanically disengaging from the first dilator when the distal terminus of the second dilator is at least substantially aligned with the distal terminus of the first dilator such that the second dilator is free to rotate about the first dilator.

2. A dilation system as recited in claim 1, further comprising:
    a second mating member formed on the interior surface of the second dilator, the second mating member being configured to engage with the first mating member when the first dilator is received within the passageway of the second dilator.

3. A dilation system as recited in claim 1, wherein the first mating member comprises an outward projecting member or a bounded track.

4. A dilation system as recited in claim 3, wherein the outward projecting member comprises a thread, thread portion, or tang.

5. A dilation system as recited in claim 2, wherein the second mating member comprises a projecting member or a bounded track.

6. A dilation system as recited in claim 1, wherein the distal insertion end of the first dilator has a tapered frustoconical configuration.

7. A dilation system as recited in claim 1, further comprising a third mating member formed on the exterior surface of the second dilator.

8. A dilation system as recited in claim 1, wherein the first dilator has a length and the second dilator has a length that is shorter than the length of the first dilator.

9. A dilation system for dilating bodily tissue, the dilation system comprising:
    an elongate first dilator comprising a tubular body having an exterior surface extending between a proximal end and an opposing distal insertion end, the body also having an interior surface bounding a passageway extending between the proximal end and the distal insertion end;
    an elongate second dilator comprising a tubular body having an exterior surface extending between a proximal end and an opposing distal insertion end, the body also having an interior surface bounding a passageway extending between the proximal end and the distal insertion end, the passageway of the second dilator being configured to receive the tubular body of the first dilator; and
    means located at the distal insertion ends of the first and second dilators for forcing the second dilator to travel along a substantially fixed path that prevents free rotation of second dilator relative to the first dilator while at least a portion of the second dilator is being advanced over the first dilator, wherein the distal insertion end of the first dilator and the second dilator each terminate at a distal terminus, the second dilator being free to rotate about the first dilator when the distal terminus of the second dilator is at least substantially aligned with the distal terminus of the first dilator.

10. A dilation system as recited in claim 9, wherein the means for forcing the second dilator to travel along a substantially fixed path comprises:

a first mating member formed on the exterior surface of the first dilator; and a second mating member formed on the interior surface of the second dilator, the second mating member being configured to engage with the first mating member when the first dilator is received within the passageway of the second dilator.

11. A dilation system as recited in claim 10, wherein:

the first mating member comprises at least one first thread outwardly projecting on the exterior surface of the first dilator; and the second mating member comprises at least one tang or at least one second thread inwardly projecting from the interior surface of the second dilator.

12. A dilation system as recited in claim 10, wherein at least a portion of the exterior surface of the first dilator on which the first mating member is formed is tapered.

13. A dilation system as recited in claim 10, further comprising a third mating member formed on the exterior surface of the second dilator.

14. A dilation system as recited in claim 9, wherein the first dilator has a length and the second dilator has a length that is shorter than the length of the first dilator.

15. A dilation system as recited in claim 9, further comprising a guide wire, the passageway of the first dilator being configured to receive the guide wire.

16. A dilation system for dilating bodily tissue, the dilation system comprising:

an elongate first dilator comprising a first tubular body having an exterior surface extending between a proximal end and an opposing distal insertion end, a first mating member formed on the exterior surface of the first tubular body at the distal insertion end, the first mating member terminating at a distal terminus; and an elongate second dilator comprising a second tubular body having an interior surface and an exterior surface, the interior surface bounding a passageway extending between a proximal end and an opposing distal insertion end, the passageway of the second tubular body being configured to receive the first tubular body, a second mating member comprising a projecting tang being formed on the interior surface of the second tubular body, the second mating member engaging with the first mating member when the first dilator is received within the passageway of the second dilator, wherein the second dilator travels along a substantially fixed path relative to the first dilator as a portion of the first dilator is advanced within the passageway of the second dilator and the first mating member engages the second mating member, and wherein the second dilator freely rotates about the first dilator when the first dilator is received within the passageway of the second dilator and the second mating member is at least substantially aligned with the distal terminus of the first mating member.

17. A dilation system as recited in claim 16, wherein the first mating member comprises a track that is at least partially bounded.

18. A dilation system as recited in claim 17, wherein the track is curved or linear.

19. A dilation system as recited in claim 16, wherein the first mating member comprises a thread, thread portion, or tang.

20. A dilation system as recited in claim 16, further comprising an elongate third dilator comprising a third tubular body having an interior surface and an exterior surface, the interior surface bounding a passageway extending between a proximal end and an opposing distal insertion end, the passageway of the third tubular body being configured to receive the second tubular body.

21. A method for dilating bodily tissue, the method comprising:

dilating bodily tissue with a distal insertion end of a first dilator;

positioning a proximal end of the first dilator within a passageway of a tubular second dilator;

advancing the second dilator over the first dilator;

mechanically engaging the second dilator with a first mating member formed at the distal insertion end of the first dilator so as to prevent free rotation of the second dilator around the first dilator through at least a portion of the advancement;

dilating bodily tissue with a distal insertion end of the second dilator; and aligning a distal terminus of the second dilator with a distal terminus of the first dilator such that the second dilator mechanically disengages from the first mating member so as to enable free rotation of the second dilator around the first dilator.

22. A method for dilating bodily tissue as recited in claim 21, further comprising advancing a third dilator over the second dilator and the first dilator.

23. A dilation system as recited in claim 16, wherein the first mating member comprises at least one thread, and wherein the second mating member is formed at the distal insertion end of the second tubular body.

* * * * *